(12) United States Patent
Wang et al.

(10) Patent No.: US 10,996,364 B2
(45) Date of Patent: May 4, 2021

(54) SYSTEM AND METHOD FOR DETERMINING WATER-FILLED POROSITY AND WATER SALINITY IN WELL CORES AND LOGS

(71) Applicant: Chevron U.S.A. Inc., San Ramon, CA (US)

(72) Inventors: Haijing Wang, Sugar Land, TX (US); Hanming Wang, Fulshear, TX (US); Emmanuel Toumelin, Houston, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 597 days.

(21) Appl. No.: 15/948,702

(22) Filed: Apr. 9, 2018

(65) Prior Publication Data

US 2018/0321412 A1 Nov. 8, 2018

Related U.S. Application Data

(60) Provisional application No. 62/501,165, filed on May 4, 2017.

(51) Int. Cl.
| | |
|---|---|
| *G01V 3/20* | (2006.01) |
| *G01V 3/32* | (2006.01) |
| *G01V 3/38* | (2006.01) |
| *G01N 27/02* | (2006.01) |

(Continued)

(52) U.S. Cl.
CPC .............. *G01V 3/20* (2013.01); *G01N 15/088* (2013.01); *G01N 27/026* (2013.01); *G01N 33/24* (2013.01); *G01V 3/32* (2013.01); *G01V 3/38* (2013.01); *G01N 2015/0853* (2013.01)

(58) Field of Classification Search
CPC ... G01V 3/32; G01V 3/38; G01V 3/20; G01N 27/026; G01N 33/24
See application file for complete search history.

(56) References Cited

U.S. PATENT DOCUMENTS 5,869,968 A * 2/1999 Brooks .................... G01V 3/30
324/338
2007/0061083 A1* 3/2007 Habashy .................. G01V 3/30
702/11

(Continued)

OTHER PUBLICATIONS

Archie, G.E, 1942, The Electrical Resistivity Log as an Aid in Determining Some Reservoir Characteristics, Paper SPE-942054-G, Transactions of the AIME, 146, 54-62. DOI/10.2118/942054-G.

(Continued)

*Primary Examiner* — Janet L Suglo
(74) *Attorney, Agent, or Firm* — Esplin & Associates, PC

(57) ABSTRACT

A method for determining water-filled porosity and water salinity in a well includes obtaining complex dielectric permittivity of earth formations, either from dielectric measurements representative of well cores, or from dielectric well logs; selecting a dielectric mixing law for the index number m; plotting a m-th root of complex dielectric permittivity at a specified frequency in the complex domain, wherein m is an index number; determining a matrix permittivity, a water salinity, and a water-filled porosity based on the complex dielectric permittivity and the dielectric mixing law; and displaying the water salinity and the water-filled porosity.

22 Claims, 11 Drawing Sheets

(51) Int. Cl.
    *G01N 15/08* (2006.01)
    *G01N 33/24* (2006.01)

(56) References Cited

U.S. PATENT DOCUMENTS

| | | | | |
|---|---|---|---|---|
| 2009/0200016 | A1* | 8/2009 | Goodwin | E21B 49/10 |
| | | | | 166/248 |
| 2013/0096833 | A1 | 4/2013 | Hanna | |
| 2017/0276832 | A1* | 9/2017 | Kouchmeshky | E21B 49/00 |
| 2018/0275307 | A1* | 9/2018 | Pan | G01V 3/32 |

OTHER PUBLICATIONS

Baker-Jarvis, J., Janezic, M.D., Domich, P.D., and Geyer, R.G, 1994, Analysis of an Open-Ended Coaxial Probe With Lift-Off for Nondestructive Testing, IEEE Transactions on Instrumentation and Measurement, 43(5), 711-718. DOI: 10.1109/19.328897.

Bittar, M., Li, J., Kainer, G., Cherry, R., Torres, D., and McCoy, D., 2010, A Modern Microwave Formation Evaluation Sensor and its Applications in Reservoir Evaluation, Paper B, Transactions, SPWLA 51st Annual Logging Symposium, Perth, Australia, Jun. 19-23. (10 pages).

Clennell, B., Dewhurst, D., and Raven, M., 2006, Shale Petrophysics: Electrical, Dielectric and Nuclear Magnetic Resonance Studies of Shales and Clays, Paper KK, Transactions, SPWLA 47th Annual Logging Symposium, Veracruz, Mexico, Jun. 4-7. (13 pages).

Clinch, S., Shafer, J., Wei, W., and Lasswell, P., 2011, Determining Formation Water Salinity in the Hydrocarbon Leg using Cores and Logs. Petrophysics, 52(2), 108-123.

Donadille, J. M., and Faivre, O., 2015, Water Complex Permittivity Model for Dielectric Logging, Paper SPE-172566 presented at the SPE Middle East Oil and Gas Show and Conference, Manama, Bahrain, Mar. 8-11. DOI: 10.2118/172566-MS. (13 pages).

Feng, S., and Sen, P.N., 1985, Geometrical Model of Conductive and Dielectric Properties of Partially Saturated Rocks, Journal of Applied Physics, 58, 3236-3243. DOI: 10.1063/1.335804.

Freed, D., Seleznev, N., Hou, C.-Y, Fellah, K., and Sen, P., 2016, A Physics-Based Model for the Dielectric Response of Shaly Sands, Paper L, Transactions, SPWLA 57th Annual Logging Symposium, Reykjavik, Iceland, Jun. 25-29. (20 pages).

Freedman, R., Rose, D., Sun, B., Brown, R.L., and Malizia, T., 2016, Novel Method for Evaluating Shale Gas and Shale Tight Oil Reservoirs Using Well Log Data, Paper SPE-181480 presented at the SPE Annual Technical Conference and Exhibition, Dubai, UAE, Sep. 26-28. DOI: 10.2118/ 181480-MS. (28 pages).

Freeman, D.W., and Henry, K.C., 1983, Improved Saturation Determination with EPT, Paper SPE-11466 presented at the Middle East Oil Technical Conference and Exhibition, Manama, Bahrain, Mar. 14-17. DOI: 10.2118/11466-MS. (8 pages).

Gavish, N., and Promislow, K., 2016, Dependence of the Dielectric Constant of Electrolyte Solutions on Ionic Concentration: A Microfield Approach, Physical Review E, 94(1), 012611. DOI: 10.1103/PhysRevE.94.012611. (7 pages).

Han, M., Cuadros, J., Suarez, C.A.P., Decoster, E., Faivre, O., Mosse, L., and Seleznev, N., 2012, Continous Estimate of Cation Exchange Capacity From Log Data: A New Approach Based on Dielectric Dispersion Analysis, Paper CC, Transactions, SPWLA 53rd Annual Logging Symposium, Cartagena, Colombia, Jun. 16-20. (15 pages).

Hizem, M., Budan, H., Deville, B., Faivre, O., Mosse, L., and Simon, M., 2008, Dielectric Dispersion: A New Wireline Petrophysical Measurement, Paper SPE-116130 presented at the SPE Annual Technical Conference and Exhibition, Denver, Colorado, USA, Sep. 21-24. DOI: 10.2118/ 116130. (21 pages).

Klein, L., and Swift, C., 1977, An Improved Model for the Dielectric Constant of Sea Water at Microwave Frequencies, IEEE Journal of Oceanic Engineering, 2(1), 104-111. DOI: 10.1109/JOE.1977.1145319.

Knight, R., and Abad, A., 1995, Rock/Water Interaction in Dielectric Properties: Experiments With Hydrophobic Sandstones, Geophysics, 60(2), 431-436. DOI: 10.1190/1.1443780.

Josh, M., Clennell, B., and Siggins, A., 2009, Practical Broadband Dielectric Measurement of Geological Samples, Paper DD, Transactions, SPWLA 50th Annual Logging Symposium, The Woodlands, Texas, USA, Jun. 21-24. (12 pages).

Meissner, T., and Wentz, F.J., 2004, The Complex Dielectric Constant of Pure and Sea Water From Microwave Satellite Observations, IEEE Transactions on Geoscience and Remote Sensing, 42(9), 1836-1849. DOI: 10.1109/TGRS.2004.831888.

Pickett, G.R., 1973, Pattern Recognition as a Means of Formation Evaluation, The Log Analyst, 1(4), 3-11.

Seleznev, N.V., Kleinberg, R.L., Herron, M.M., Machlus, M., Pomerantz, A.E., Reeder, S.L., Burnham, A.K., Day, R.L., and Allix, P.C., 2011, Applications of Dielectric Dispersion Logging to Oil Shale Reservoirs, Paper G, Transactions, SPWLA 52nd Annual Logging Symposium, 1Colorado Springs, Colorado, May 4-18. (16 pages).

Seleznev, N.V., Habashy, T.M., Boyd, A.J., and Hizem, M., 2006, Formation Properties Derived From a Multi-Frequency Dielectric Measurement, Paper VVV, Transactions, SPWLA 47th Annual Logging Symposium, Veracruz, Mexico, Jun. 4-7. (12 pages).

Seleznev, N.V., Fellah, K., Phillips, J., Zulkipli, S.N.,and Fournie, B., 2016, Matrix Permittivity Measurements for Rock Powders, Paper SPE-170896, SPE Reservoir Evaluation and Engineering, 19(2), 214-225. DOI: 10.2118/170896-PA.

Seleznev, N., Boyd, A., Habashy, T., and Luthi, S.M., 2004, Dielectric Mixing Laws for Fully and Partially Saturated Carbonate Rocks, Paper CCC, Transactions, SPWLA 45th Annual Logging Symposium, Noordwijk, Netherlands, Jun. 6-9. (14 pages).

Sen, P.N., 1980, The Dielectric and Conductivity Response of Sedimentary Rocks, Paper SPE-9379 presented at the SPE Annual Technical Conference and Exhibition, Dallas, Texas, Sep. 21-24. DOI: 10.2118/9379-MS. (11 pages).

Shehab, F., Myers, M.T., Ott, H., Dolan, S., Dietderich, J., and Bayazitoglu, Y., 2017, Uniaxial Complex Relative Permittivity Tensor Measurement of Rocks From 40 Hz to 4.5 GHz. IEEE Transactions on Geoscience and Remote Sensing, 55(2), 1125-1139. DOI: 10.1109/TGRS.2016.2620078.

Stroud, D., Milton, G.W., and De, B.R., 1986, Analytical Model for the Dielectric Response of Brine-Saturated Rocks, Physical Review B, 34, 5145-5153. DOI: 10.1103/PhysRevB.34.5145.

Taherian, M.R., Yuen, D.J., Habashy, T.M., and Kong, J.A., 1991, A Coaxial-Circular Waveguide for Dielectric Measurement, IEEE Transactions on Geoscience and Remote Sensing, 29(2), 321-330. DOI: 10.1109/36.73675.

Toumelin, E., Torres-Verdin, C., and Bona, N., 2008, Improving Petrophysical Interpretation With Wide-Band Electromagnetic Measurements, Paper SPE-96258, SPE Journal, 13(2), 205-215. DOI: 10.2118/96258-PA.

Wang, H., and Poppitt, A., 2013, The Broadband Electromagnetic Dispersion Logging Data in a Gas Shale Formation: A Case Study, Paper AAA, Transactions, SPWLA 54th Annual Logging Symposium, New Orleans, Louisiana, USA, Jun. 22-26. (12 pages).

Worthington, P.F., 1985, The Evolution of Shaly-sand Concepts in Reservoir Evaluation, The Log Analyst, 26(1), 23-40.

Zhang, T., Al-Ofi , S., and Akbar, M., 2012, Error Quantification of a Plug Scale Lab Dielectric Spectroscopy Setup and its Application in Material Characterization, Progress in Geophysics, 27(2), 582-595.

* cited by examiner

US 10,996,364 B2

SYSTEM AND METHOD FOR DETERMINING WATER-FILLED POROSITY AND WATER SALINITY IN WELL CORES AND LOGS

CROSS-REFERENCE TO RELATED APPLICATIONS

The present Application claims the benefit of and priority to U.S. Provisional Application No. 62/501,165 filed on May 4, 2017, the contents of which are incorporated herein in their entirety.

FIELD

Embodiments of the present disclosure relate generally to hydrocarbon well core and log analysis, in particular, to systems and methods of determining water-filled porosity and water salinity in well cores and logs.

BACKGROUND

The oil and gas industry provides important sources of energy needed for the world's economic growth, by exploring and producing petroleum liquid and gas from subsurface reservoirs. Reservoir quality may be quantified by the total volume of hydrocarbon stored in a reservoir prior to production, also known as original hydrocarbon in place (OHIP). Recoverable reserve may also be used as a reservoir quality indicator. Recoverable reserve is the portion of reserve that can be profitably produced with existing extraction technology. Accurate estimations of reserve (original oil in place OOIP/original gas in place OGIP) and recovery reserve may be used to optimize reservoir management and achieve the most favorable economic outcome.

Formation evaluation supplies the parameters needed for reserve estimation, such as pay thickness (fraction of a given fluid within the total pore volume occupied by all fluids), porosity, saturation, and permeability. Saturation is the volume of petroleum fluids in relative to the total pore volume available in reservoir rocks, in which petroleum fluid can be water, oil, or gas. A number of downhole well logging and laboratory characterization techniques have been developed and implemented to quantify water saturation, with the rest of pore volume occupied by hydrocarbons.

SUMMARY

Embodiments of the present disclosure provide a method of determining water-filled porosity and water salinity in a well including obtaining complex dielectric permittivity of earth formations, either from dielectric measurements representative of well cores, or from dielectric well logs; selecting a dielectric mixing law for the index number m; and plotting a m-th root of complex dielectric permittivity at a specified frequency in the complex domain, wherein m is an index number. Some embodiments include, selecting a different dielectric mixing law or a different index number m; determining a matrix permittivity, a water salinity, and a water-filled porosity based on the complex dielectric permittivity and the dielectric mixing law; and using the water salinity and the water-filled porosity to make decisions about how to complete the well and other reservoir management decisions is disclosed.

Some embodiments of the present disclosure provide a non-transitory computer readable storage medium storing one or more programs. The one or more programs comprise instructions, which when executed by a computer system with one or more processors and memory, cause the computer system to perform any of the methods provided herein.

Some embodiments of the present disclosure provide a computer system. The computer system includes one or more processors, memory, and one or more programs. The one or more programs are stored in memory and configured to be executed by the one or more processors. The one or more programs include an operating system and instructions that when executed by the one or more processors cause the computer system to perform any of the methods provided herein.

These and other objects, features, and characteristics of the system and/or method disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

Figure 1:
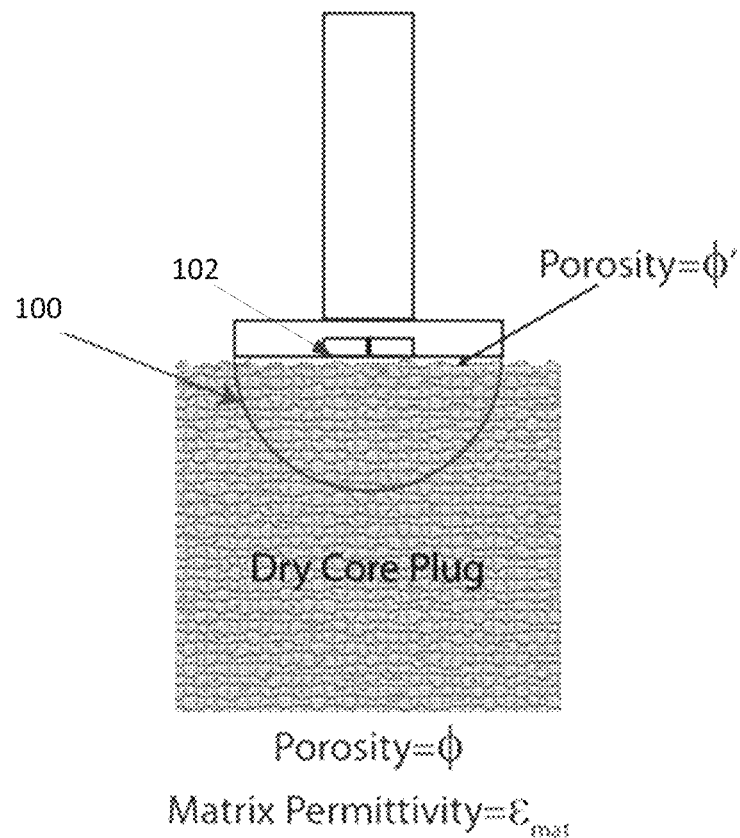
FIG. 1 illustrates a dielectric probe used to take dielectric measurements of a well core, consistent with embodiments disclosed herein.

The figures are not intended to be exhaustive or to limit the invention to the precise form disclosed. It should be understood that the disclosed technology can be practiced with modification and alteration, and that the disclosed technology be limited only by the claims and the equivalents thereof.

DETAILED DESCRIPTION

Embodiments of the present disclosure provide systems and methods for well core and log analysis. Reference will now be made in detail to various embodiments, examples of which are illustrated in the accompanying drawings. In the following detailed description, numerous specific details are set forth in order to provide a thorough understanding of the present disclosure and the embodiments described herein. However, embodiments described herein may be practiced without these specific details. In other instances, well-known methods, procedures, components, and mechanical apparatus have not been described in detail so as not to unnecessarily obscure aspects of the embodiments.

Measuring resistivity is a well logging technique that may be used to determine saturation, e.g., as a part of the neutron-density-resistivity "triple-combo". Resistivity logging measures the resistivity or conductivity of the formation and the water saturation as calculated in clay-free rock formation, e.g., using Equation 1 described below.

$$S_w = \sqrt[n]{\frac{a \cdot R_w}{\phi^m \cdot R_t}} \quad (1)$$

As used in Equation 1, $S_w$ represents water saturation, $\phi$ represents porosity, $R_w$ represents formation water resistivity, $R_t$ represents measured formation resistivity, a is a constant, m represents a cementation factor, and n represents a saturation exponent. In some examples, a may be about 1. In some examples, m may be about 2, or may vary around a center point of 2. In some examples, n may be about 2. Porosity may be determined from neutron-density or nuclear magnetic resonance logs. The rest of parameters used in Equation 1 may be inferred from knowledge of the field or reasonable assumptions for a particular interval. For instance, $R_w$ may be estimated by resistivity readings from a previously observed fully water-saturated zone or from water samples. Selection of appropriate values of m and n may be accomplished using techniques known in the art, e.g., using a Pickett plot. If water salinity can be determined, a corresponding Rw may be directly calculated at certain temperature. This method is based on the assumption that the salinity is a constant within the interval of interest. A difference in water salinity across different zones, or between water and hydrocarbon leg, may introduce error in water saturation.

The relationships described by Equation 1 may be empirically determined and verified using samples from clay-free sand formations. In shaly-sand formations, clay minerals may provide additional contribution to conductivity, which is not accounted for in Equation 1. In such examples, shaly-sand equations may be used to correct for the clay contribution to conductivity and to improve the accuracy of water saturation estimation. In carbonate rock formations, m and n may vary due to complex pore systems and affinity of rock surface to oil rather than water. These factors prompt challenges in water saturation determination.

Dielectric and nuclear logging, under favorable conditions can provide water saturation estimation that is independent of Equation 1. Dielectric logging is based on the fact that the dielectric constant (real part of complex dielectric permittivity in relative to that of vacuum) of water is in the range of 45 to 80, depending on salinity and temperature, while those of rock and hydrocarbon are about 5 and 2, respectively. Dielectric logging makes it possible to determine the water-filled porosity without having to know water salinity.

Using a multi-frequency dielectric logging tool may further allow the elucidation of textural distribution and formation factor. However, the depth of investigation of dielectric logging may be effective for just a few inches within the formation, which means that its measurement is affected by the drilling fluid which invades the permeable formation and flushes out the native formation fluids. As a result, the measured flushed-zone water salinity may not be relevant to the formation water salinity. From pulsed neutron logging tools, total neutron capture cross-section (Sigma) and carbon-oxygen measurements may provide an estimation of water saturation under favorable conditions.

The Sigma of formation water depends on its salinity, driving by the large sigma value of chloride, serving as the contrast between water and hydrocarbon. Sigma can provides a reasonably good water saturation estimate when the porosity is larger than 15% and salinity is larger than 50 parts-per-thousand. Carbon-oxygen logging may provide the ratio of carbon and oxygen, which may be converted into water saturation. Carbon-oxygen logging uses slow logging speed (a few feet per minute) to obtain sufficiently high neutron counting statistics.

Chloride content as determined from neutron-gamma spectroscopy may also be used to determine fresh water salinity, although such log data may include some significant statistical uncertainty. Uncertainty in well log interpretation may be reduced by laboratory characterization of rock and fluid samples extracted from subsurface formations. Core plugs, properly handled and preserved after extraction, may be characterized in the laboratory for water saturation and salinity.

Methods for determining formation water properties may be based on the extraction of water and salt from the core plug. For instance, in one example method, correlation from additional anion and cation produced by mineral dissolution and mineral reaction may be used and the results corrected for clay-bound water. Water may be extracted by centrifuging core samples. However, produced water may be reduced below actual saturation levels when water saturation is close to an irreducible water level, preventing accurate measurement of its volume and salinity.

Formation water resistivity may also be determined by the complex resistivity measurement of core plugs, without having to extract brine or salt. This method may be based on the measurement of capacitance at two frequencies on preserved cores, and an empirical correlation between the capacitance ratio or the "salinity index" and formation water resistivity. This method does not require extraction of water and salt from core plugs.

Embodiments disclosed herein provide of a method and system for dielectric measurement and interpretation methods using a portable broadband apparatus and complex-domain analysis of mixing laws for water-filled porosity and water salinity in porous media. Example methods include (1) measuring complex dielectric permittivity of core plugs by continuous frequency sweeping over a broadband of frequency range, (2) measuring and interpreting relative dielectric permittivity of matrix (matrix permittivity) on non-preserved or cleaned core plugs based on dielectric measurement on the core plug saturated with brine of previously observed salinity and the same core vacuum-dried at elevated temperature, and (3) non-destructively measuring and interpreting fresh or preserved core plugs using complex-domain analysis of mixing laws to determine water-filled porosity and salinity. The complex-domain analysis of mixing laws is not limited to core analysis, and may also be implemented for log interpretation.

An example dielectric measurement apparatus may include a dielectric probe to couple electronics with core samples, a vector network analyzer (VNA) or impedance analyzer for generating frequency sweep and recording response signal, software to convert the signal to real and imaginary components of dielectric permittivity. In some examples, the disclosed apparatus may include a Dielectric Assessment Kit System (DAKS). The apparatus may include an end-loaded dielectric probe connected to a portable VNA such as vector reflectometer. In some examples, the system may include a remote power source, e.g., a USB port or a battery, allowing it to be used in the laboratory or a wellsite without a standard AC electric supply. The apparatus may also include a standard AC or DC power supply. In some examples the frequency range of the example apparatus may cover multiple frequencies, including frequency ranges used for dielectric logging. Example probes may include a vector reflectometer for continuous frequency sweep over their respective frequency range, and data acquisition software for converting electric reflectance to real and imaginary part of dielectric permittivity.

In some embodiments, the apparatus may be used to take a dielectric measurement, e.g., by pressing the dielectric probe against a flat surface of a core plug. For example, the flat surface may be an end of a cylindrical core plug or the ends of any section cut from the a core barrel. For example, the core plug may have a diameter ranging from about ½ inch to several inches. A section of whole core contained in a core barrel may a diameter of 4 inch and length of 3 feet. Using a core barrel section may enable taking a dielectric measurement at the wellsite to avoid any mud invasion or water loss during core handling and transportation. In some examples, the dielectric measurement may be taken while the environment in which the measurement is taken has a stable (e.g., non-varying temperature, within an acceptable range), and the temperature may be recorded.

Some embodiments include determining matrix permittivity on non-preserved or cleaned core plugs based on a dielectric measurement of the core plug re-saturated with brine of a known salinity. The example method may include vacuum-drying the core. The example method may include vacuum-drying the core at an elevated temperature. For core plugs that are not preserved or have already been cleaned, formation fluids may have already been partially or completely displaced, making direct measurements of water saturation and salinity less effective. However, under the same conditions, matrix permittivity of the core remains unchanged. Matrix permittivity may be used as an input parameter to determine water saturation for log interpretation. In some examples, an error of 1 unit in matrix permittivity may result in an error of about a 5% to about 15% in saturation unit for 20% porosity core plugs. The dielectric log may be calibrated to compensate for this error using measured matrix permittivity.

FIG. 1 is a diagram of dielectric apparatus 100 used to take a dielectric measurement of a well core. In some examples, dielectric apparatus 100 may include a dielectric probe. Dielectric apparatus 100 may include a dielectric sensor 102. In some examples, a dielectric apparatus may include a dielectric probe and a signal generator (not shown). For example, the signal generator may be a frequency sweep signal generator and/or a VNA. In some examples, dielectric probe 100 may be an end-loaded probe.

As illustrated in the example shown in FIG. 1, the surface of the core plug may not be smooth or provide sufficient contact with the flat surface of dielectric probes. In such cases, air gaps between core plugs and dielectric probe surface may add systematic error in the measurement. In addition, the core plug may have its own porosity, which may be filled with dry air. Thus, measuring the complex dielectric permittivity on a dry core plug may be an effective representative value for the mixture of the air gap, the air in porosity, and the matrix itself. In some examples, dielectric apparatus 100 may also include logical circuits, e.g., a porosity and salinity logical circuit, as disclosed herein.

Figure 2:
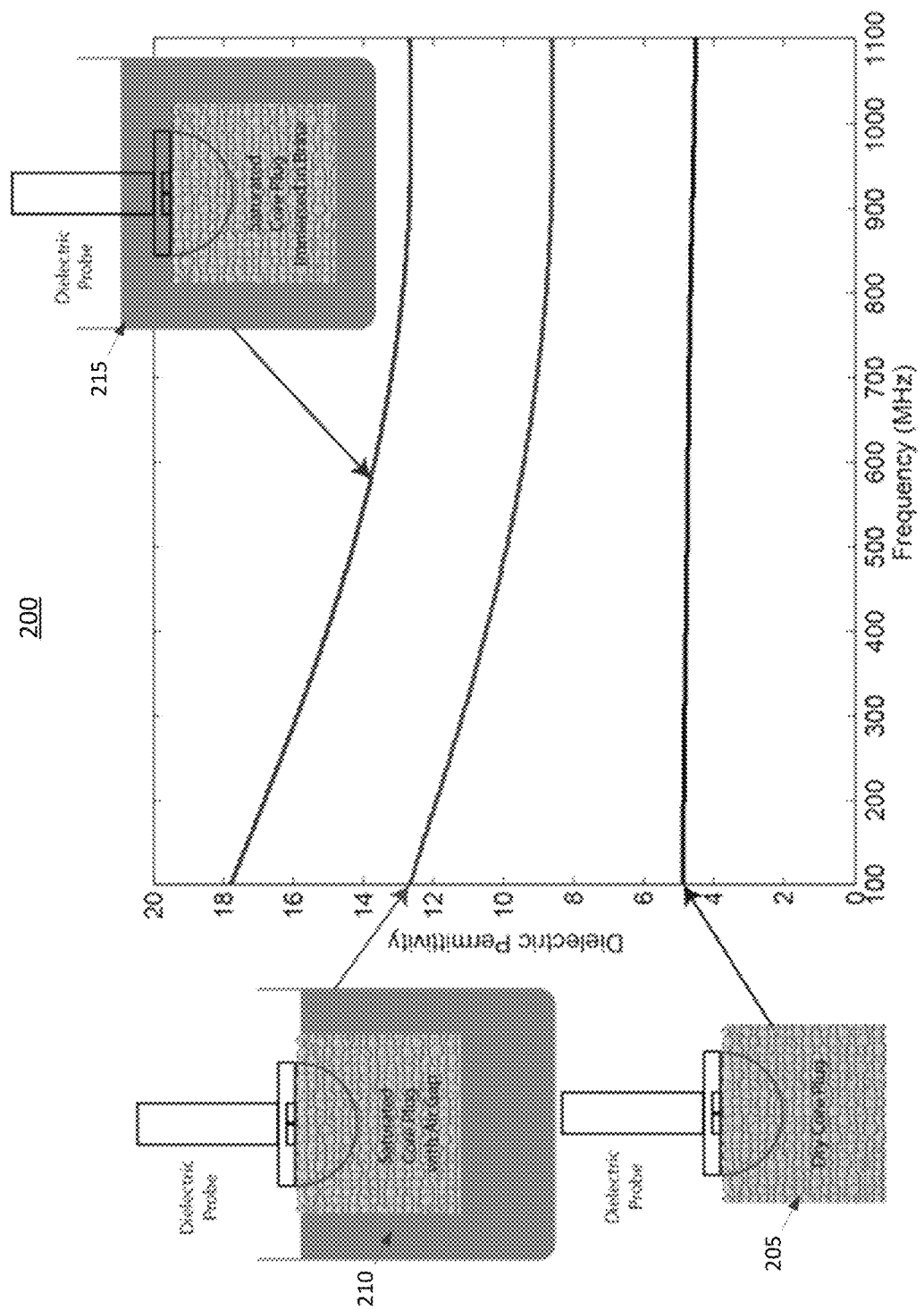
FIG. 2 is a diagram of a method for an example multi-step measurement to improve the accuracy of end-loaded dielectric probe, consistent with embodiments disclosed herein.

FIG. 2 illustrates an example multi-step measurement method 200 may be used to reduce systematic errors due to air gaps and account for the porosity effect. In some examples, the multi-step measurement method 200 may include three steps. For example, three measurements may be used to assist in solving for three unknown parameters: (1) effective porosity due to air gap ($\phi'$) at step 205; (2) total porosity ($\phi$) at step 210; and (3) matrix permittivity ($\varepsilon_{mat}$) at step 215, all of which are real numbers. In some examples, the method may include measuring and solving for two of these three parameters. The multi-step measurements of complex dielectric permittivity may be performed on the same core plug at different saturation states: dry core plug $\varepsilon_{dry}^*$, brine-saturated core plug with measurement surface exposed to air $\varepsilon_{open}^*$, and brine-saturated core plug immersed in brine $\varepsilon_{imm}^*$. Based on one of the mixing laws or dielectric dispersion models, the three unknowns may be solved as:

$$[\phi', \phi\varepsilon_{mat}] = f(\varepsilon_{dry}^*, \varepsilon_{open}^*, \varepsilon_{imm}^*) \quad (2)$$

For instance, the mixing law may include a complex refractive index method (CRIM). In some examples, the complex dielectric permittivity of air-brine-matrix mixture may be described by:

$$\sqrt{\varepsilon_{dry}^*} = (1-\phi') \cdot \phi \cdot \sqrt{\varepsilon_{air}} + (1-\phi') \cdot (1-\phi) \cdot \sqrt{\varepsilon_{mat}} + \phi' \cdot \sqrt{\varepsilon_{air}}$$

$$\sqrt{\varepsilon_{open}^*} = (1-\phi') \cdot \phi \cdot \sqrt{\varepsilon_{wat}} + (1-\phi') \cdot (1-\phi) \cdot \sqrt{\varepsilon_{mat}} + \phi' \cdot \sqrt{\varepsilon_{air}}$$

$$\sqrt{\varepsilon_{imm}^*} = (1-\phi') \cdot \phi \cdot \sqrt{\varepsilon_{wat}} + (1-\phi') \cdot (1-\phi) \cdot \sqrt{\varepsilon_{mat}} + \phi' \cdot \sqrt{\varepsilon_{wat}} \quad (3)$$

The total porosity $\phi$ may be used as a quality control term by comparing dielectric-determined porosity with porosity determined by routine core analysis methods. When the mineral composition of the core plug is available, i the measured matrix permittivity may be compared with that calculated from its mineral composition using:

$$\varepsilon_{mat} = (\Sigma \psi_i \sqrt{\varepsilon_i})^2 \quad (4)$$

where $\Sigma \psi_i = 1$ is volumetric mineral composition, $\varepsilon_i$ is relative dielectric permittivity of each mineral. An example database of some selected mineral dielectric permittivity values is illustrated in Table 1 below.

TABLE 1

Example Relative Dielectric Permittivity Values for Example Minerals

|  | Material | $\varepsilon_r$ |
|---|---|---|
| [Table 1. Replaced]→ | Sandstone | 4.65 |
|  | Limestone | 7.5~9.2 |
|  | Anhydrite | 6.35 |
|  | Clay dry colloids | 5.6~6.35 |
|  | Gypsum | 4.16 |

Some embodiments include performing non-destructive measurements and interpretations on fresh or preserved core plugs for water-filled porosity and salinity, without having to extract formation fluids. The disclosed methods address measurement challenges caused by formation water and oil in the pore space of fresh or well-preserved core plugs, difficulties in re-saturating the core plug with brine of known salinity, in order to preserve the formation fluids for other measurement on the same core plug, and unknown matrix permittivity at the time due to a pore fluid effect.

For example, a CRIM expression of the CRIM function for the preserved core plugs may be represented as:

$$\sqrt{\varepsilon_{eff}^*} = (1-\phi_T)\sqrt{\varepsilon_{mat}} + \phi_w\sqrt{\varepsilon_{wat}^*(Sal_w,T)} + \phi_0\sqrt{\varepsilon_{oil}} + \phi_g\sqrt{\varepsilon_{gas}} \quad (5)$$

Equation 5 includes too many unknowns ($\phi_T$, $\varepsilon_{mat}$, $\phi_w$, $Sal_w$, $\phi_a$, $\phi_g$) to solve with one measurement (2 equations for real and imaginary part). Here $\varepsilon_{wat}^*(Sal_w,T)$ may represent the complex permittivity of water as a function of salinity and temperature at certain frequency.

Figure 3:
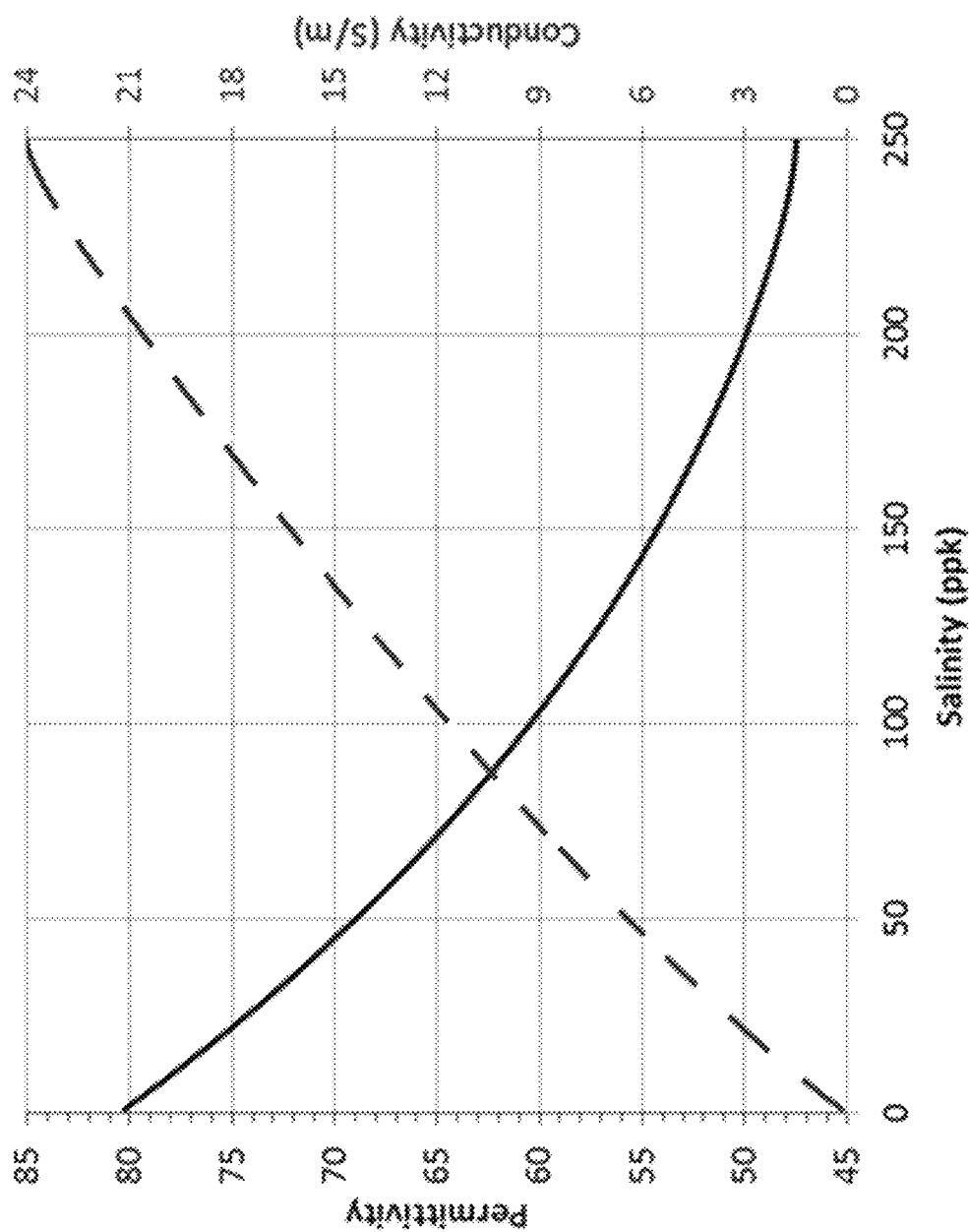
FIG. 3 is a graph of relative dielectric permittivity (shown as solid line) and conductivity (shown as dashed line) of water as function of salinity at room temperature.

FIG. 3 illustrates the dielectric permittivity and conductivity of water as functions of salinity at room temperature. In some examples, parameters may be obtained from other well logs and simplify Equation 5. For instance, $\varepsilon_{mat}$ can be calculated from mineral composition or estimated by the expected lithology (e.g., $\varepsilon_{mat}$=4.65 for sandstone). If $\phi_T$ is not available, then it may be set as $\phi_T=\phi_w$ and the last two terms may be removed, because of the large difference between dielectric permittivity of water and the rest of terms. Thus, the CRIM equation may be approximated as:

$$\sqrt{\varepsilon_{eff}^*} = (1-\phi_w)\sqrt{\varepsilon_{mat}} + \phi_w\sqrt{\varepsilon_{wat}^*(Sal_w,T)} \quad (6)$$

Figure 4:
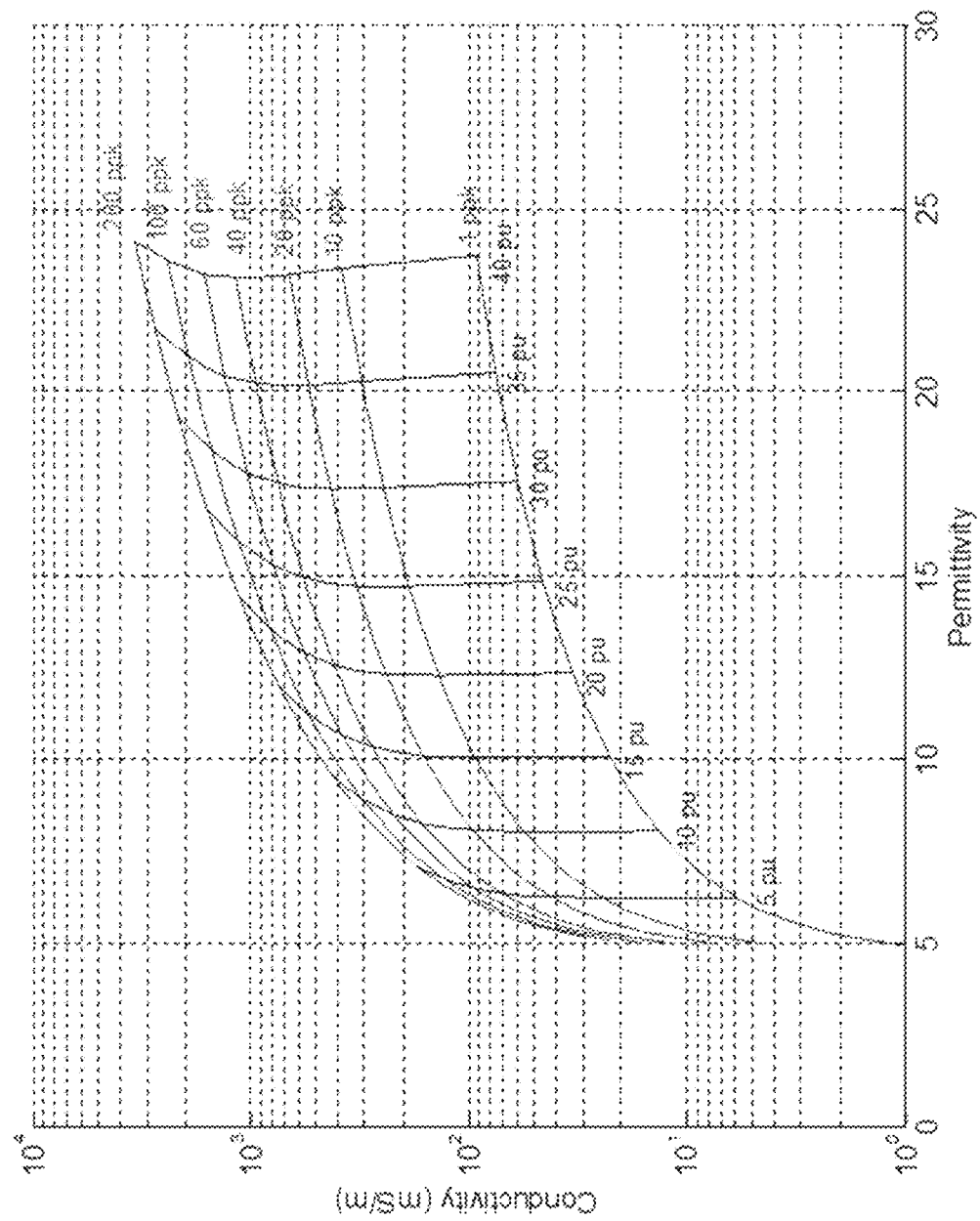
FIG. 4 is a dielectric interpretation chart.

As shown in Equation 6, simplified CRIM equation has two unknowns ($\phi_w$, $Sal_w$) and two equations (real and imaginary). It is therefore possible to convert measured permittivity and conductivity into water-filled porosity and salinity. However, the assumptions to simply the CRIM equation may add systematic errors to the interpretation, particularly for salinity. The simplification ignores the effect of oil and air, which may shift the entire interpretation chart in FIG. 4, leading to large error in salinity, particularly in the low water-filled porosity region.

Some embodiments of the method are implement the relationships described below, e.g., starting with Equation 7:

$$\sqrt{\varepsilon_{eff}^*} = (1-\phi_t)\cdot\sqrt{\varepsilon_{mat}} + \phi_w\sqrt{\varepsilon_{wat}} + \phi_w\sqrt{\varepsilon_{wat}^*} + \phi_0\sqrt{\varepsilon_{oil}} + \phi_g\sqrt{\varepsilon_{gas}} \quad (7)$$

The non-water contributions may be grouped together with the effective dielectric permittivity into one "matrix effective" term as illustrated in Equation 8:

$$(1-\phi_w)\cdot\sqrt{\varepsilon_{mat\_eff}} = (1-\phi_t)\cdot\sqrt{\varepsilon_{mat}} + \phi_0\cdot\sqrt{\varepsilon_{oil}} + \phi_g\sqrt{\varepsilon_{gas}} \quad (8)$$

All terms in Equation 8 may be real numbers, to simplify the equations to the expression in Equation 9.

$$\sqrt{\varepsilon_{eff}^*} = (1-\phi_w)\cdot\sqrt{\varepsilon_{mat\_eff}} + \phi_w\sqrt{\varepsilon_{wat}^*} \quad (9)$$

Equation 9 may be reorganized as Equation 10:

$$\phi_w = \frac{\sqrt{\varepsilon_{eff}^*} - \sqrt{\varepsilon_{mat\_eff}}}{\sqrt{\varepsilon_{wat}^*} - \sqrt{\varepsilon_{mat\_eff}}} \quad (10)$$

If CRIM is valid, the water-filled porosity should be a real number, which also means that the vector determined by the complex number $\sqrt{\varepsilon_{eff}^*}-\sqrt{\varepsilon_{mat\_eff}}$ and $\sqrt{\varepsilon_{wat}^*}-\sqrt{\varepsilon_{matt\_eff}}$ should be in parallel, e.g., $\sqrt{\varepsilon_{eff}^*}$ may be used to connect $\sqrt{\varepsilon_{mat\_eff}}$ and $\sqrt{\varepsilon_{wat}^*}$ in the complex domain.

Figure 5:
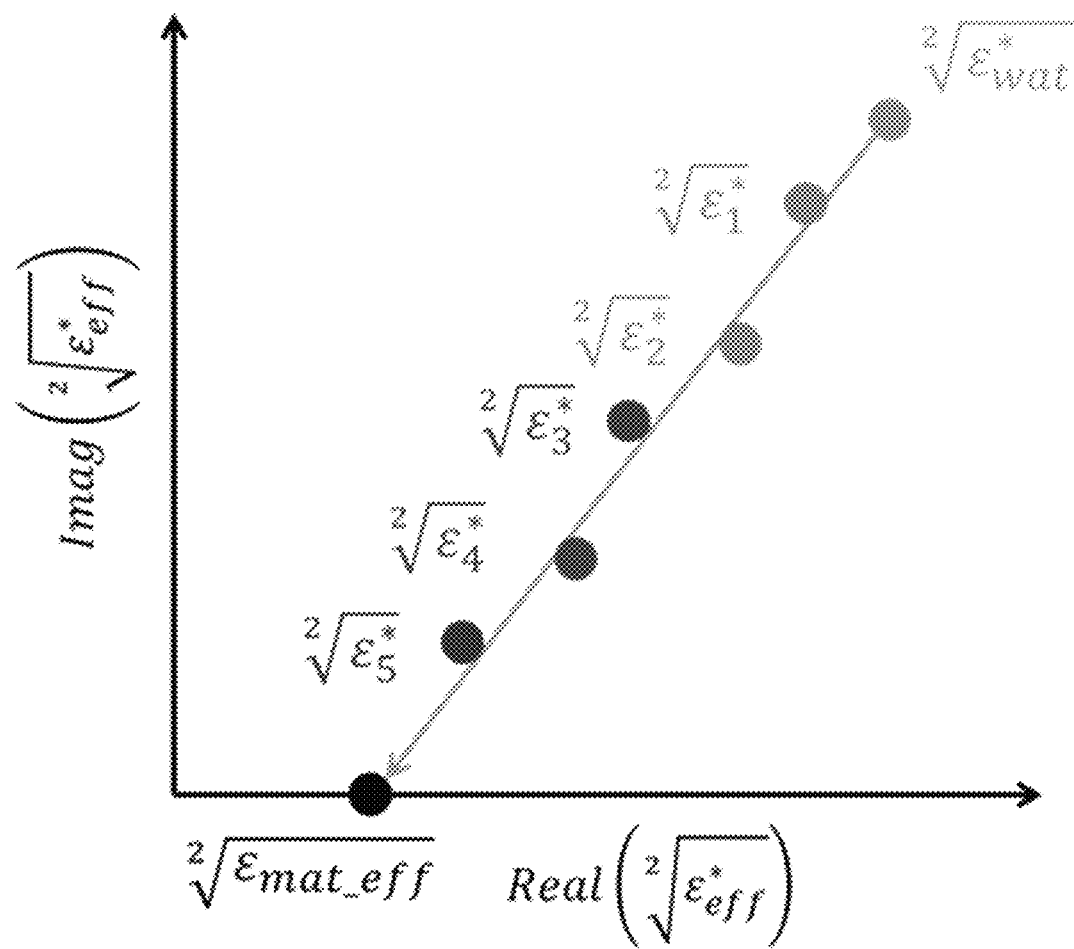
FIG. 5 is a graph of complex-domain analysis and solution of the complex refractive index mixing (CRIM) equation.

FIG. 5 shows the complex-domain analysis and solution for the CRIM equation, with all measured $\sqrt{\varepsilon_{eff}^*}$ on one line connecting $\sqrt{\varepsilon_{mat\_eff}}$ and $\sqrt{\varepsilon_{wat}^*}$ in the complex domain.

Example dielectric measurements may be obtained (e.g., $\varepsilon_1^*, \ldots, \varepsilon_5^*$) on different positions of the same preserved core plug, and a regression may be applied to data points ($^2\sqrt{\varepsilon_1^*}, \ldots, ^2\sqrt{\varepsilon_5^*}$) plotted in the complex domain. The intercept of this line with real axis may be represented $\sqrt{\varepsilon_{mat\_eff}}$, and the intercept on the other side with the water permittivity line may be used to determine the salinity. The water permittivity line may be constructed by plotting complex water permittivity as function of salinity in the complex domain. The water-filled porosity of each data point may be represented as a ratio of two lengths, $|\sqrt{\varepsilon_{eff}^*}-\sqrt{\varepsilon_{mat\_eff}}|$ and $|\sqrt{\varepsilon_{wat}^*}-\sqrt{\varepsilon_{mat\_eff}}|$. In some examples, the regression method used to plot the lines may include a least-mean square regression, or other regression methods as known in the art.

Figure 6A:
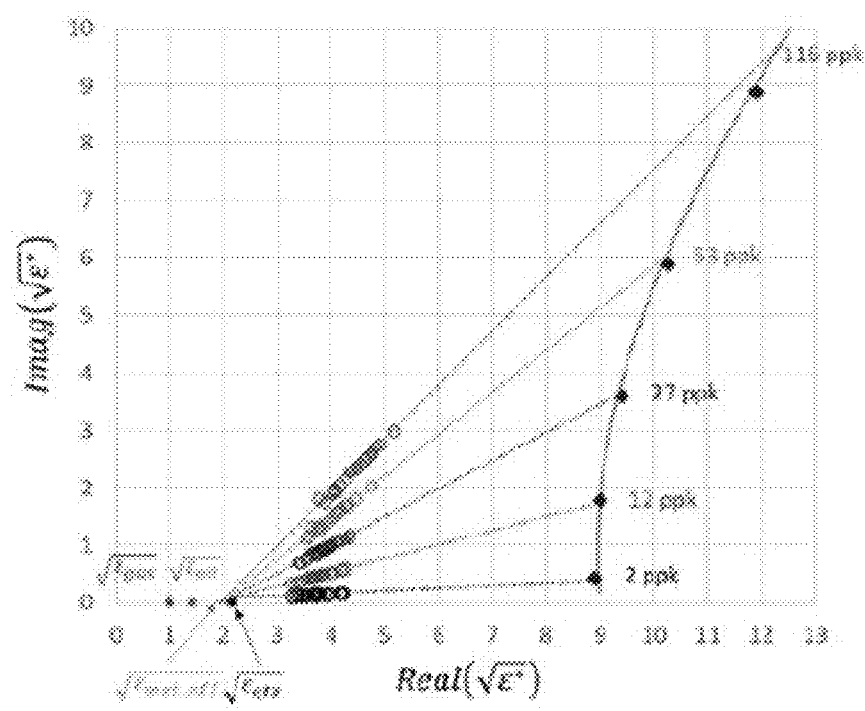
FIG. 6A is a graph of complex-domain analysis and solution of the CRIM equation for 5 sandstone core plugs.
Figure 6B:
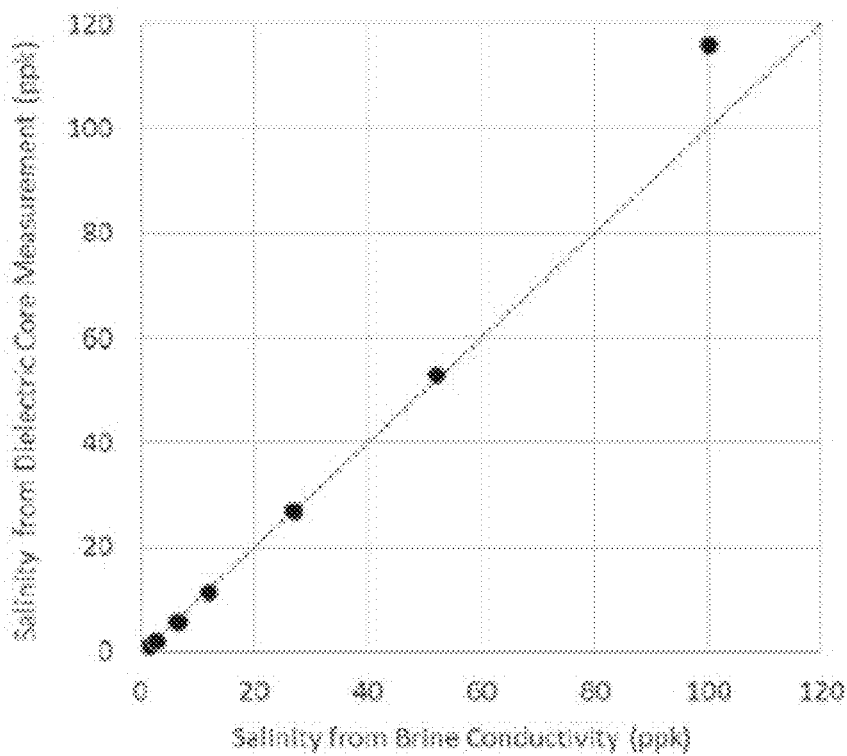
FIG. 6B is a graph comparing the salinity determined from dielectric core measurement and salinity determined from the conductivity of bulk brine.

In an example application of the method disclosed above, 5 sandstone core plugs were obtained with different porosity with a wide range of brine salinity (NaCl salt, 1~100 ppk). For each brine salinity, the complex dielectric permittivity was measured on both surfaces of core plugs. On each surface, one measurement was taken when the core plugs are immersed in the brine, and another with the surface exposed to air. For each salinity value, 4 data points were acquired at each core plug, e.g., 20 data points for 5 core plugs. Because of similar matrix property, all 20 points at each salinity value in the complex square root of the complex dielectric permittivity ($\sqrt{\varepsilon_{eff}^*}$) fell on a straight line as shown in FIG. 6. The line at each salinity was extended to the real axis to obtain $\sqrt{\varepsilon_{mat\_eff}}$, between $\sqrt{\varepsilon_{oil}}$ and $\sqrt{\varepsilon_{mat}}$. Extending these lines to the water permittivity curve, salinity values can be determined. FIG. 6B compares the salinity determined from dielectric core measurement with that determined from the conductivity of bulk brine. They agree very well. The small mismatch difference at 116 ppk is because the conductivity of bulk brine exceeds the measurement limit of the dielectric probe. The water-filled porosity and salinity were determined based on the measured data points in complex domain, without assuming input parameters.

Figure 7:
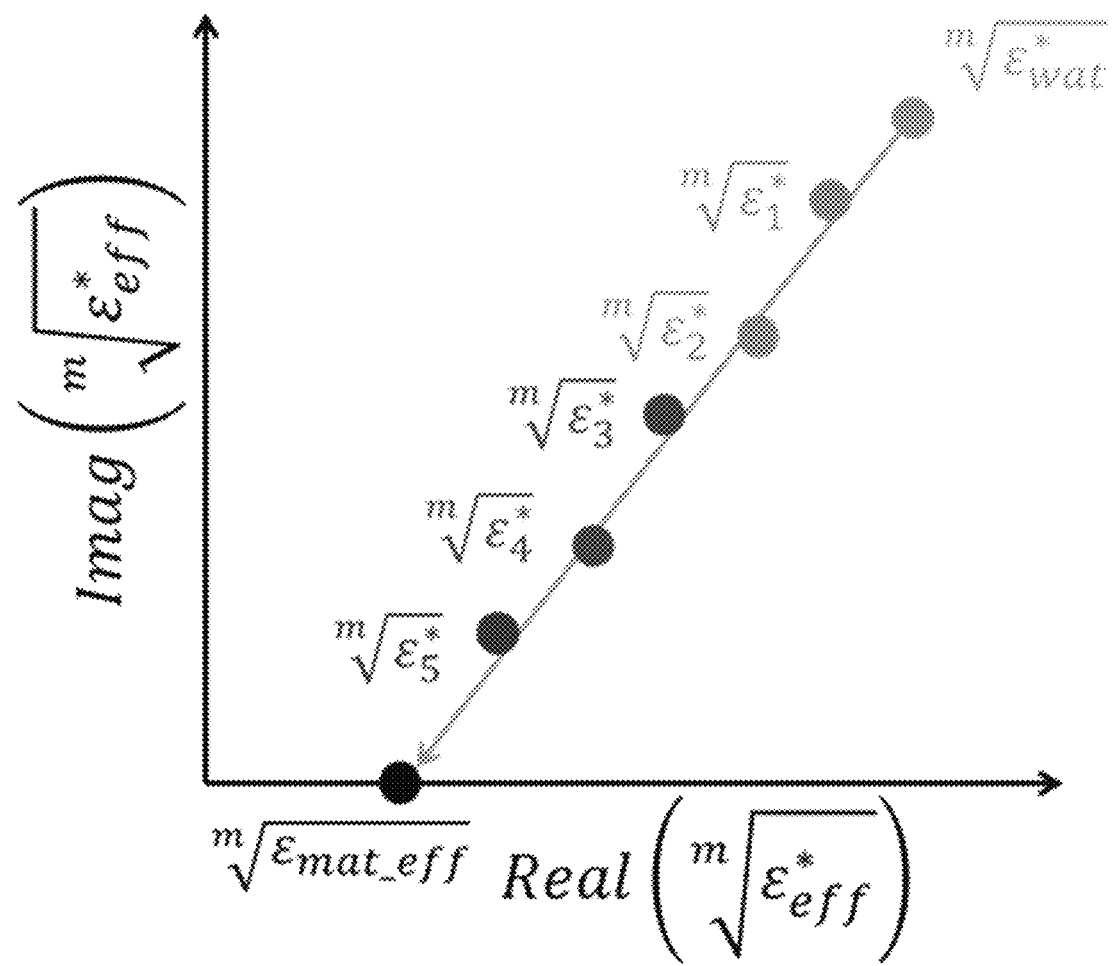
FIG. 7 is a graph of complex-domain analysis and solution of a general dielectric mixing law.

Example mixing laws are provided in Table 2. With reference to table 2, the index may be any real number. The mixing laws may be applied to both core data and log data. FIG. 7 illustrates a plot of $^m\sqrt{\varepsilon_{eff}^*}$ in the complex domain for mixing laws with index m for data with similar salinity and similar lithology applying the relationship in Equation 11.

$$\phi_w = \frac{\sqrt[m]{\varepsilon_{eff}^*} - \sqrt[m]{\varepsilon_{mat\_eff}}}{\sqrt[m]{\varepsilon_{wat}^*} - \sqrt[m]{\varepsilon_{mat\_eff}}} \quad (11)$$

Water-filled porosity and salinity can be determined similar to above as shown in FIG. 5. The same interpretation method may be applied to log data without having to know the matrix permittivity as an input.

TABLE 2

Dielectric mixing laws with different indeces

| Index | Mixing Laws |
|---|---|
| $m = -1$ | $(\varepsilon_{eff}^*)^{-1} = \sum_{n=1}^{N} \phi_n \cdot (\varepsilon_n^*)^{-1}$ |
| $m = 1$ | $\varepsilon_{eff}^* = \sum_{n=1}^{N} \phi_n \cdot \varepsilon_n^*$ |
| $m = 2$ | $(\varepsilon_{eff}^*)^{\frac{1}{2}} = \sum_{n=1}^{N} \phi_n \cdot (\varepsilon_n^*)^{\frac{1}{2}}$ |
| $m = 3$ | $(\varepsilon_{eff}^*)^{\frac{1}{3}} = \sum_{n=1}^{N} \phi_n \cdot (\varepsilon_n^*)^{\frac{1}{3}}$ |
| $m \to \infty$ | $\ln(\varepsilon_{eff}^*) = \sum_{n=1}^{N} \phi_n \cdot \ln(\varepsilon_n^*)$ |

Figure 8A:
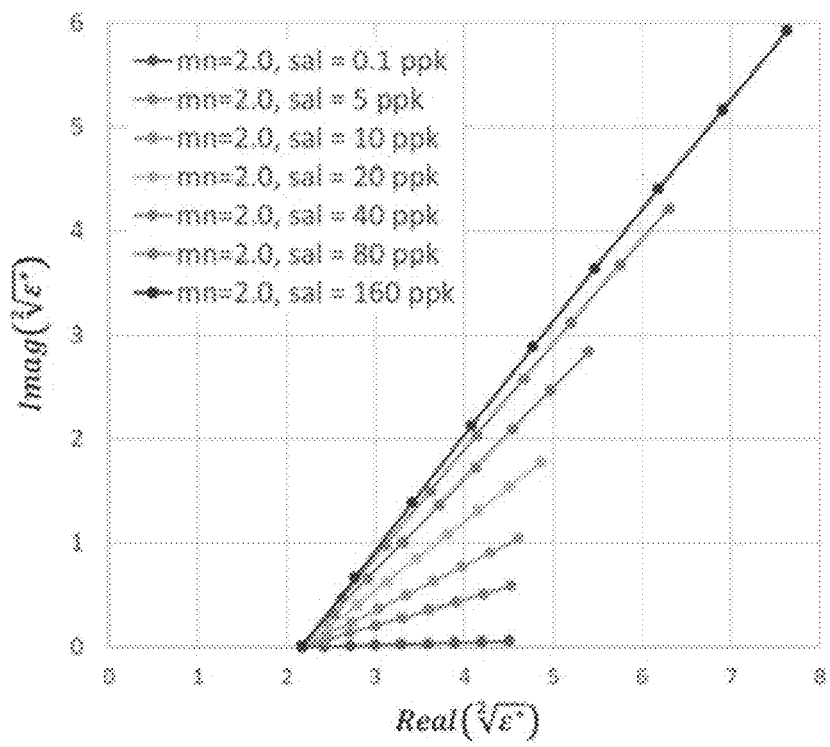
FIGS. 8A, 8B, and 8C illustrate an example application of the disclosed methods on example forward-modeled complex dielectric permittivity data based on a Stroud-Milton-De (SMD) model.
Figure 8B:
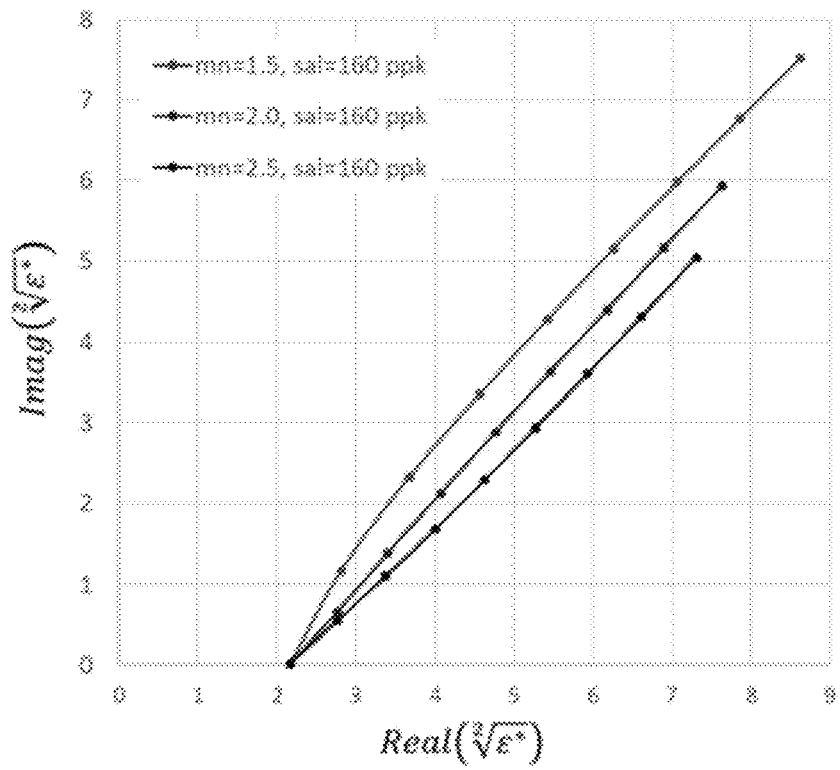
Figure 8C:
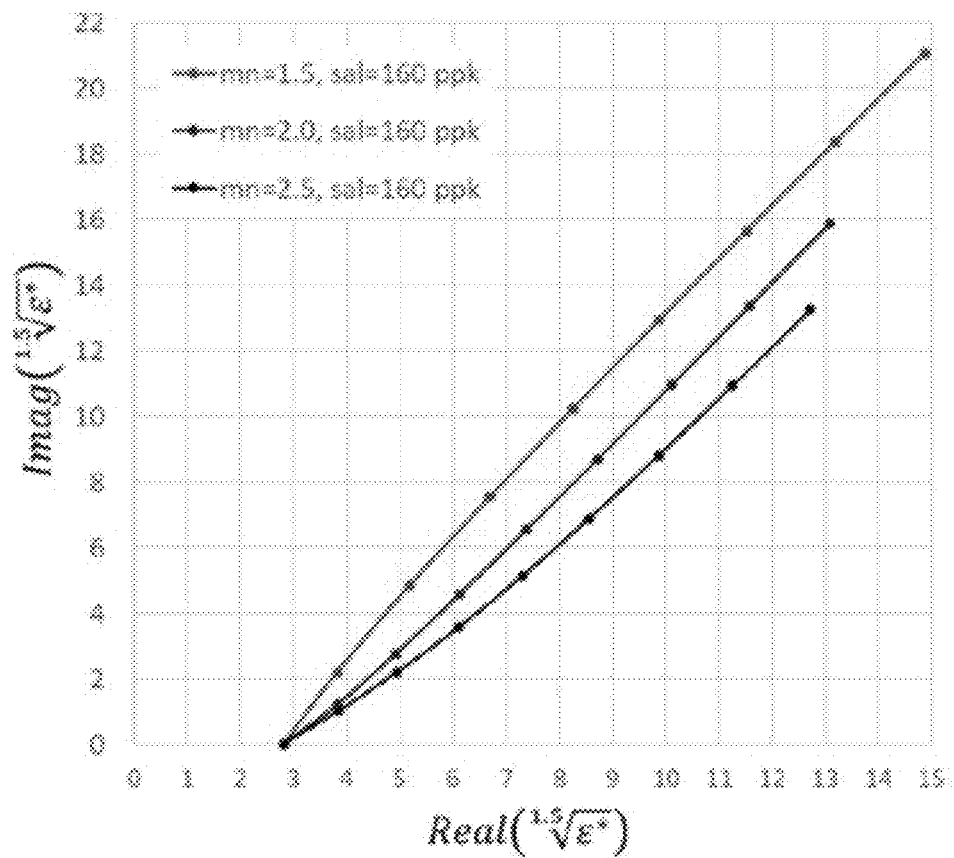

Some example mixing laws are provided by the SMD model. FIGS. 8A, 8B, and 8C illustrate an example application of the disclosed methods on example forward-modeled complex dielectric permittivity data based on SMD model. In the example illustrated in FIG. 8, $\varepsilon_{mat}$ is assumed to be 4.65, temperature T is assumed to be 120 degrees Fahrenheit, and total porosity is assumed to be filled with water and varying from 0.1 to 40 p.u. In the illustrated example, the textural information is parameterized as mn, which is equivalent to the case of m=n in Equation 1. In FIG. 8A, the example modeled data is based on a textural information parameter mn=2.0. The example data is plotted on a CDA cross-plot between the imaginary and real part of $^2\sqrt{\varepsilon\varepsilon^*}$. The iso-salinity lines in FIG. 8A demonstrate linearity for a wide range of salinity, e.g., from about 0.1 to about 160 ppk, all intercepting with the real axis at $\sqrt{\varepsilon_{mat\_eff}}$.

FIG. 8B refers to the same example described above with respect to FIG. 8A. FIG. 9B illustrates that if the index of CDA cross-plot $^2\sqrt{\varepsilon^*}$ does not match mn=1.5 or 2.5 used to generate the dielectric data, the relationship becomes non-linear for high salinity and low porosity, and the linear portion of the line extending to the real axis does not intercept with $\sqrt{\varepsilon_{mat\_eff}}$. The example illustrates the effect of textural information which can be observed from the scattering of dielectric permittivity data.

FIG. 8C refers to the same example described above with respect to FIGS. 8A and 8B. As illustrated in FIG. 8C, the relationship becomes more linear using an index of CDA cross-plot $^{1.5}\sqrt{\varepsilon^*}$ with the mn=1.5 value used to generate the example dielectric data. As illustrated by this example, selection of the index m may be used to improve linearity, i.e., by selecting a m value that results in a distribution of $^m\sqrt{\varepsilon^*}$ being populated closely around a straight line in the complex domain.

The most appropriate index m for a given circumstance can be selected by plotting dielectric data set obtained from same salinity and similar lithology in the form of $^m\sqrt{\varepsilon^*}$ with a range of index m in the complex domain. The most appropriate m value will be the one that makes the distribution of $^m\sqrt{\varepsilon^*}$ populated closely around a straight line in the complex domain. This interpretation method can be applied to log data without having to know the matrix permittivity as an input, as long as there is enough variation in water-filled porosity, and similar lithology, texture, and salinity. Water-filled porosity, effective matrix permittivity, and salinity can be determined similarly, as shown in FIG. 5. These methods can be combined with electro-facies or other rock classification scheme and numerical algorithms to generate a matrix permittivity log directly from dielectric logs, which will be very useful for dielectric interpretation immediately after logging or in the presence of simple logging suites without enough logs to resolve multimineral analysis.

Figure 9:
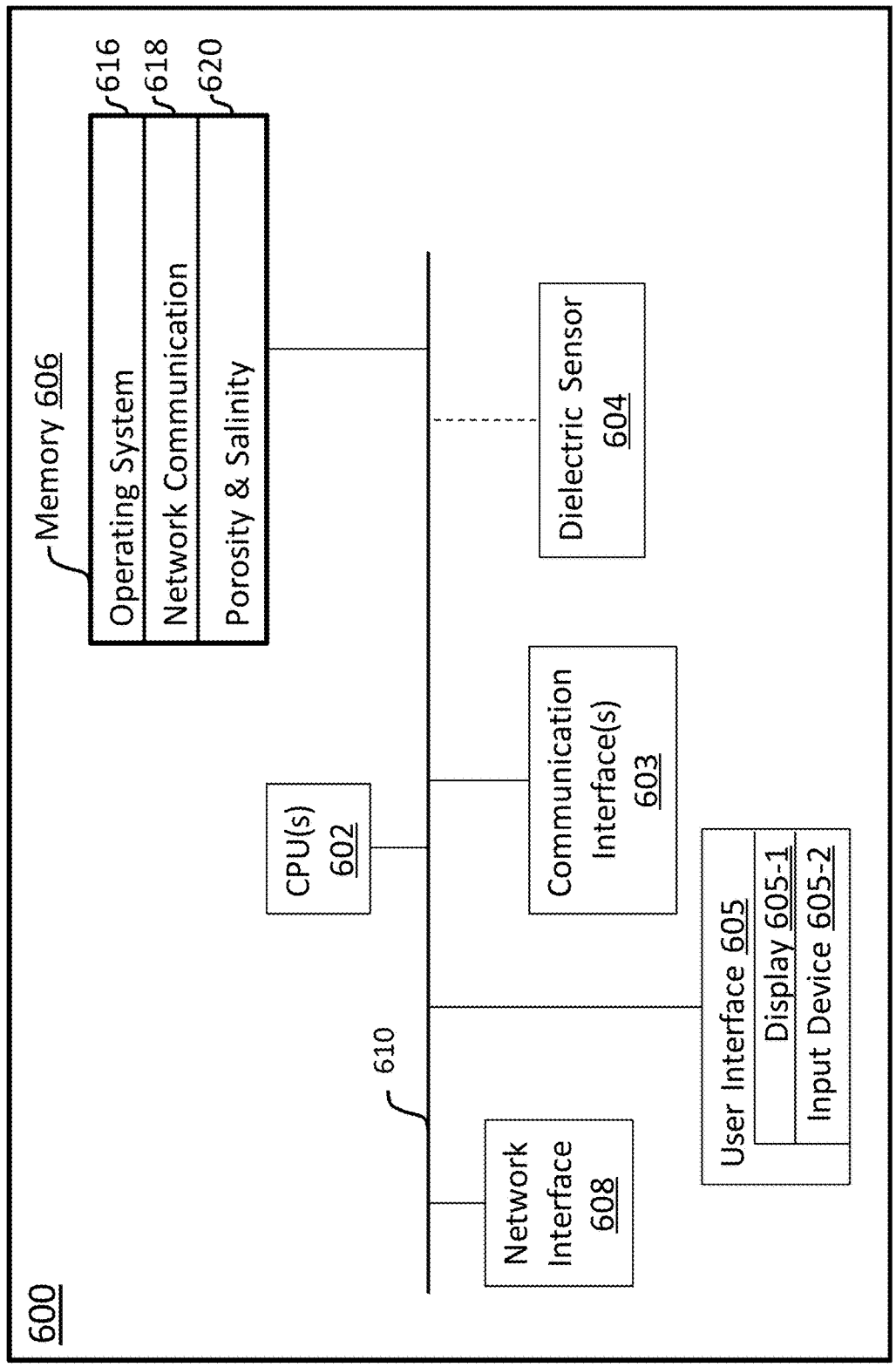
FIG. 9 is a block diagram illustrating a fault seal prediction system, in accordance with some embodiments.

FIG. 9 is a block diagram illustrating a well core and well log analysis system 600 used to implement well core and well log analysis methods, as disclosed herein. While certain specific features are illustrated, those skilled in the art will appreciate from the present disclosure that various other features have not been illustrated for the sake of brevity and so as not to obscure more pertinent aspects of the embodiments disclosed herein.

Referring to FIG. 9, a well core and well log analysis system 600 includes one or more processing units (CPUs) 602, one or more network interfaces 608 and/or other communications interfaces 603, memory 606, and one or more communication buses 610 for interconnecting these and various other components. The well core analysis system 600 may also include a user interface 605 (e.g., a display 605-1 and an input device 605-2). In some examples, user interface 605 includes a graphical user interface (GUI). The well core analysis system 600 may optionally include the dielectric sensor 604. Dielectric sensor 604 may be, e.g., a dielectric probe. In some examples, dielectric measurements may be acquired from a well core sample using dielectric sensor 604. In some embodiments, dielectric measurements may be stored in a well log (e.g., in memory 606) and system 600 may be used to analyze the well log data. The communication buses 610 may include circuitry (sometimes called a chipset) that interconnects and controls communications between system components. Memory 606 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 606 may optionally include one or more storage devices remotely located from the CPUs 602. Memory 606, including the non-volatile and volatile memory devices within memory 606, comprises a non-transitory computer readable storage medium and may store a variety of petrophysical data including dielectric permittivity measurements. The dielectric permittivity measurements may be transmitted to the memory 606 from the dielectric probe 604, through the network interface 608, through the communications interface(s) 603, or through the user interface 605.

In some embodiments, memory 606 or the non-transitory computer readable storage medium of memory 606 stores the following programs, logical circuits and data structures, or a subset thereof including an operating system 616, a network communication logical circuit 618, and a porosity and salinity logical circuit 620.

The operating system 616 includes procedures for handling various basic system services and for performing hardware dependent tasks.

The network communication logical circuit 618 facilitates communication with other devices via the communication network interfaces 608 (wired or wireless) and one or more communication networks, such as the Internet, other wide area networks, local area networks, metropolitan area networks, and so on.

Although the porosity and salinity logical circuit 620 is portrayed as a single logical circuit, this is not meant to be limiting. It may consist of a number of logical circuits configured to execute operations needed for the embodiments described herein, and may contain other instructions, metadata, and parameters that allow it to execute other operations of use in calculating the water-filled porosity and water salinity. The porosity and salinity logical circuit 620 may optionally be able to generate a display that would be sent to and shown on the user interface display 605-1. In addition, any of the data products may be transmitted via the communication interface(s) 603 or the network interface 608 and may be stored in memory 606.

The embodiments described herein are, optionally, governed by instructions that are stored in computer memory or a non-transitory computer readable storage medium (e.g., memory 606 in FIG. 9) and are executed by one or more processors (e.g., processors 602) of one or more computer systems. The computer readable storage medium may include a magnetic or optical disk storage device, solid state storage devices such as flash memory, or other non-volatile memory device or devices. The computer readable instructions stored on the computer readable storage medium may include one or more of: source code, assembly language code, object code, or another instruction format that is interpreted by one or more processors. In various embodiments, some operations in each method may be combined and/or the order of some operations may be changed from the order shown in the figures. For ease of explanation, the method is described as being performed by a computer system, although in some embodiments, various operations of the method are distributed across separate computer systems.

Those skilled in the art will appreciate that the disclosed embodiments described herein are by way of example only, and that numerous variations will exist. The invention is limited only by the claims, which encompass the embodiments described herein as well as variants apparent to those skilled in the art. In addition, it should be appreciated that structural features or method steps shown or described in any one embodiment herein can be used in other embodiments as well.

Figure 10:
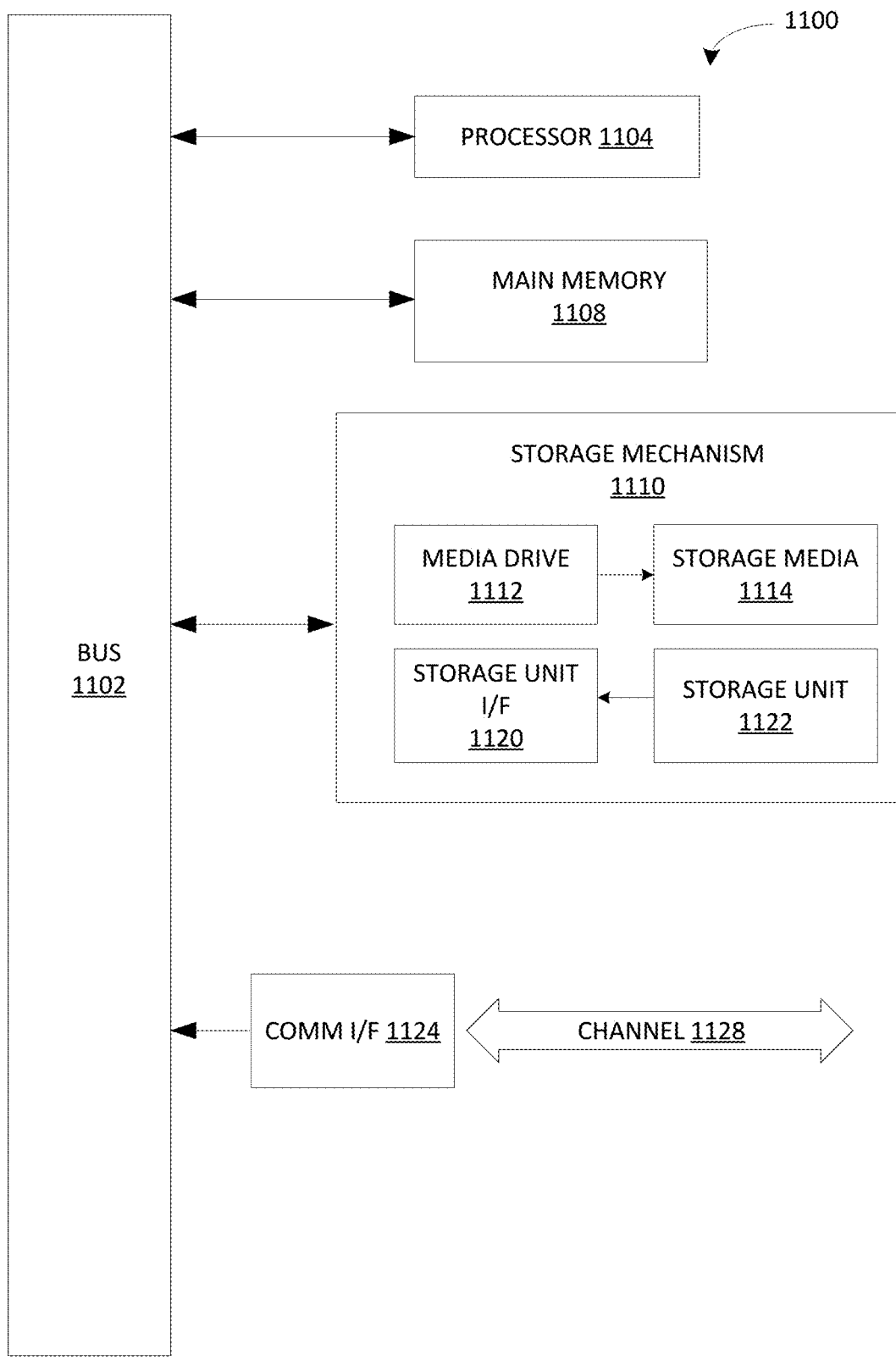
FIG. 10 illustrates an example computing system that may be used in implementing various features of embodiments of the disclosed technology.

As used herein, the terms logical circuit and component might describe a given unit of functionality that can be performed in accordance with one or more embodiments of the technology disclosed herein. As used herein, either a logical circuit or a component might be implemented utilizing any form of hardware, software, or a combination thereof. For example, one or more processors, controllers, ASICs, PLAs, PALs, CPLDs, FPGAs, logical components, software routines or other mechanisms might be implemented to make up a component. In implementation, the various components described herein might be implemented as discrete components or the functions and features described can be shared in part or in total among one or more components. In other words, as would be apparent to one of ordinary skill in the art after reading this description, the various features and functionality described herein may be implemented in any given application and can be implemented in one or more separate or shared components in various combinations and permutations. Even though various features or elements of functionality may be individually described or claimed as separate components, one of ordinary skill in the art will understand that these features and functionality can be shared among one or more common software and hardware elements, and such description shall not require or imply that separate hardware or software components are used to implement such features or functionality.

Where components, logical circuits, or components of the technology are implemented in whole or in part using software, in one embodiment, these software elements can be implemented to operate with a computing or logical circuit capable of carrying out the functionality described with respect thereto. One such example logical circuit is shown in FIG. 10. Various embodiments are described in terms of this example logical circuit 1100. After reading this description, it will become apparent to a person skilled in the relevant art how to implement the technology using other logical circuits or architectures.

Referring now to FIG. 10, computing system 1100 may represent, for example, computing or processing capabilities found within desktop, laptop and notebook computers; hand-held computing devices (PDA's, smart phones, cell phones, palmtops, etc.); mainframes, supercomputers, workstations or servers; or any other type of special-purpose or general-purpose computing devices as may be desirable or appropriate for a given application or environment. Logical circuit 1100 might also represent computing capabilities embedded within or otherwise available to a given device. For example, a logical circuit might be found in other electronic devices such as, for example, digital cameras, navigation systems, cellular telephones, portable computing devices, modems, routers, WAPs, terminals and other electronic devices that might include some form of processing capability.

Computing system 1100 might include, for example, one or more processors, controllers, control components, or other processing devices, such as a processor 1104. Processor 1104 might be implemented using a general-purpose or special-purpose processing component such as, for example, a microprocessor, controller, or other control logic. In the illustrated example, processor 1104 is connected to a bus 1102, although any communication medium can be used to facilitate interaction with other components of logical circuit 1100 or to communicate externally.

Computing system 1100 might also include one or more memory components, simply referred to herein as main memory 1108. For example, preferably random access memory (RAM) or other dynamic memory, might be used for storing information and instructions to be executed by processor 1104. Main memory 1108 might also be used for storing temporary variables or other intermediate information during execution of instructions to be executed by processor 1104. Logical circuit 1100 might likewise include a read only memory ("ROM") or other static storage device coupled to bus 1102 for storing static information and instructions for processor 1104.

The computing system 1100 might also include one or more various forms of information storage mechanism 1110, which might include, for example, a media drive 1112 and a storage unit interface 1120. The media drive 1112 might include a drive or other mechanism to support fixed or removable storage media 1114. For example, a hard disk drive, a floppy disk drive, a magnetic tape drive, an optical disk drive, a CD or DVD drive (R or RW), or other removable or fixed media drive might be provided. Accordingly, storage media 1114 might include, for example, a hard disk, a floppy disk, magnetic tape, cartridge, optical disk, a CD or DVD, or other fixed or removable medium that is read by, written to or accessed by media drive 1112. As these examples illustrate, the storage media 1114 can include a computer usable storage medium having stored therein computer software or data.

In alternative embodiments, information storage mechanism 1110 might include other similar instrumentalities for allowing computer programs or other instructions or data to be loaded into logical circuit 1100. Such instrumentalities might include, for example, a fixed or removable storage unit 1122 and an interface 1120. Examples of such storage units 1122 and interfaces 1120 can include a program cartridge and cartridge interface, a removable memory (for example, a flash memory or other removable memory component) and memory slot, a PCMCIA slot and card, and other fixed or removable storage units 1122 and interfaces 1120 that allow software and data to be transferred from the storage unit 1122 to logical circuit 1100.

Logical circuit 1100 might also include a communications interface 1124. Communications interface 1124 might be used to allow software and data to be transferred between logical circuit 1100 and external devices. Examples of communications interface 1124 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 1124 might typically be carried on signals, which can be electronic, electromagnetic (which includes optical) or other signals capable of being exchanged by a given communications interface 1124. These signals might be provided to communications interface 1124 via a channel 1128. This channel 1128 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 1108, storage unit 1120, media 1114, and channel 1128. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the logical circuit 1100 to perform features or functions of the disclosed technology as discussed herein.

Although FIG. 10 depicts a computer network, it is understood that the disclosure is not limited to operation with a computer network, but rather, the disclosure may be practiced in any suitable electronic device. Accordingly, the computer network depicted in FIG. 10 is for illustrative purposes only and thus is not meant to limit the disclosure in any respect.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent component names other than those depicted herein can be applied to the various partitions.

Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "component" does not imply that the components or functionality described or claimed as part of the component are all configured in a common package. Indeed, any or all of the various components of an component, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A computer-implemented method of determining water-filled porosity and water salinity in a well, the method comprising:
    applying a dielectric apparatus to a well core, the dielectric apparatus comprising a dielectric probe, and a frequency sweep signal generator;
    generating, with the frequency sweep signal generator, a broadband signal over a selected frequency range;
    obtaining, from the dielectric probe, a complex dielectric permittivity of the well core in response to the broadband signal;
    selecting a dielectric mixing law with the index number m;
    calculating m-th root of complex dielectric permittivity over the selected frequency range;
    plotting, on a graphical user interface (GUI), a m-th root of complex dielectric permittivity over the selected frequency range in a complex domain, wherein m is an index number;
    determining, with a porosity and salinity logical circuit, a matrix permittivity, a water salinity, and a water-filled porosity based on the complex dielectric permittivity and the dielectric mixing law, wherein the water salinity is determined further by crossing of a linear regression fit of the m-th root of complex dielectric permittivity with a water line in the complex domain; and
    displaying the water salinity and the water-filled porosity on the GUI.

2. The method of claim 1, wherein the selected frequency range is between about 1 KHz and about 10 GHz.

3. The method of claim 1, wherein the frequency sweep signal generator comprises a vector network analyzer (VNA), a vector reflectometer, or an impedance analyzer.

4. The method of claim 1, wherein the well core comprises a brine-saturated well core or a dry well core.

5. The method of claim 1, wherein the index number m is about 2 and represents a complex refractive index method.

6. The method of claim 1, wherein plotting a m-th root of complex dielectric permittivity over the selected frequency range in a complex domain comprises generating a cross-plot of an imaginary component as a function of a real component of the m-th root of complex dielectric permittivity.

7. The method of claim 6, further comprising grouping multiple dielectric permittivity measurements based on lithology and salinity.

8. The method of claim 1, wherein the selecting of the dielectric mixing law comprises performing a linear regression fit of the m-th root of complex dielectric permittivity in the complex domain.

9. The method of claim 8, further comprising selecting a second dielectric mixing law based on the linear regression and determining, with a porosity and salinity logical circuit, the matrix permittivity, the water salinity, and the water-filled porosity based on the complex dielectric permittivity and the second dielectric mixing law.

10. The method of claim 1, wherein determining the matrix permittivity comprises determining an effective matrix permittivity, wherein the effective matrix permittivity is a function of the matrix permittivity, a water saturation, and a total porosity.

11. The method of claim 10, further comprising determining a m-th root of effective matrix permittivity by performing a linear regression fit of the m-th root of complex dielectric permittivity and identifying an intercept with a real axis in the complex domain.

12. The method of claim 1, further comprising generating the water line by plotting the complex dielectric permittivity of water as function of salinity at the selected frequency range and a selected temperature.

13. The method of claim 1, further comprising determining the water-filled porosity by taking a ratio of two distances from the plot of the m-th root of complex dielectric permittivity.

14. The method of claim 13, wherein a numerator of the ratio is the distance between points representing dielectric permittivity of the rock and effective matrix permittivity.

15. The method of claim 13, wherein a denominator of the ratio is the distance between points representing effective matrix permittivity and a crossing of linear regression fit of m-th root of complex dielectric permittivity with a water line in the complex domain.

16. A system for determining water-filled porosity and water salinity in a well, the system comprising:
    a dielectric apparatus comprising a dielectric probe, a frequency sweep signal generator, a porosity and salinity logical circuit, and a graphical user interface;
    wherein the frequency sweep signal generator is configured to generate a broadband signal over a selected frequency range; and
    the porosity and salinity logical circuit comprises a processor and a non-transitory medium with computer executable instructions embedded thereon, the computer executable instructions configured to:
    obtain a complex dielectric permittivity from a dielectric probe applied to a well core or from well logs stored in a memory;
    select a dielectric mixing law with the index number m;
    calculate an m-th root of complex dielectric permittivity over the selected frequency range;
    plot, on the graphical user interface (GUI), a m-th root of complex dielectric permittivity over the selected frequency range in a complex domain, wherein m is an index number;
    determine a matrix permittivity, a water salinity, and a water-filled porosity based on the complex dielectric permittivity and the dielectric mixing law, wherein the water salinity is determined further by crossing of a linear regression fit of the m-th root of complex dielectric permittivity with a water line in the complex domain; and
    display the water salinity and the water-filled porosity on the GUI.

17. The system of claim 16, wherein the selected frequency range is between about 1 KHz and about 10 GHz.

18. The system of claim 17, wherein the frequency sweep signal generator comprises a vector network analyzer (VNA), a vector reflectometer, or an impedance analyzer.

19. The system of claim 16, wherein the well core comprises a brine-saturated well core or a dry well core.

20. The system of claim 16, wherein the computer executable instructions are further configured to cause the processor to store the dielectric measurement in a well log and determine the dielectric permittivity from the well log.

21. The system of claim 16, wherein the index number m is about 2 and represents a complex refractive index method.

22. The system of claim 16, wherein the computer executable instructions are further configured to cause the processor to generate the water line by plotting the complex dielectric permittivity of water as function of salinity at the selected frequency range and a selected temperature.

* * * * *